(12) United States Patent
Soltanian

(10) Patent No.: US 10,624,627 B2
(45) Date of Patent: Apr. 21, 2020

(54) IMPLANTABLE FASCIAL APPROXIMATOR

(71) Applicant: University Hospitals Cleveland Medical Center, Cleveland, OH (US)

(72) Inventor: Hooman Soltanian, Bloomfield, CT (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 202 days.

(21) Appl. No.: 15/508,599

(22) PCT Filed: Sep. 3, 2015

(86) PCT No.: PCT/US2015/048370
§ 371 (c)(1),
(2) Date: Mar. 3, 2017

(87) PCT Pub. No.: WO2016/036959
PCT Pub. Date: Mar. 10, 2016

(65) Prior Publication Data
US 2017/0290580 A1 Oct. 12, 2017

Related U.S. Application Data

(60) Provisional application No. 62/046,241, filed on Sep. 5, 2014.

(51) Int. Cl.
A61B 17/04 (2006.01)
A61B 17/08 (2006.01)
A61B 17/00 (2006.01)

(52) U.S. Cl.
CPC ...... *A61B 17/0466* (2013.01); *A61B 17/0401* (2013.01); *A61B 17/08* (2013.01);
(Continued)

(58) Field of Classification Search
CPC . A61B 17/0401; A61B 17/0466; A61B 17/08; A61B 2017/0414; A61B 17/04;
(Continued)

(56) References Cited

U.S. PATENT DOCUMENTS

| 5,127,412 A | 7/1992 | Cosmetto et al. |
| 6,120,525 A * | 9/2000 | Westcott ............ A61B 17/0466 606/216 |

(Continued)

FOREIGN PATENT DOCUMENTS

| RU | 116 334 U1 | 5/2012 |
| SU | 927236 A | 5/1982 |

OTHER PUBLICATIONS

International Search Report from Corresponding Application No. PCT/US2015/048370; dated Feb. 4, 2016.

*Primary Examiner* — Ryan J. Severson
*Assistant Examiner* — Mohamed G Gabr
(74) *Attorney, Agent, or Firm* — Pearne & Gordon LLP

(57) ABSTRACT

Any of a number of implantable or partially implantable approximators, including, but not limited to, manual and ratchet approximators using a tensioning component that can be at least partially provided within a wound for closing the fascia of a wound (such as around the approximatoor) using continuously tensioned sutures. Also provided are approximators with automatic tensioning features, including electrically driven devices.

4 Claims, 5 Drawing Sheets

(52) U.S. Cl.
CPC .............. *A61B 2017/00022* (2013.01); *A61B 2017/00734* (2013.01); *A61B 2017/0414* (2013.01); *A61B 2017/0464* (2013.01); *A61B 2017/0496* (2013.01); *A61B 2017/081* (2013.01)

(58) Field of Classification Search
CPC .......... A61B 17/00234; A61B 17/0642; A61B 2017/0464; A61B 2017/0496; A61B 2017/081; A61B 2017/00022; A61B 2017/0073; A61B 2017/0404; A61B 2017/0456; A61B 2017/0488; A61F 2250/0004; A61F 2250/0012; A61F 2/0045

See application file for complete search history.

(56) References Cited

U.S. PATENT DOCUMENTS

| | | |
|---|---|---|
| 7,429,265 B2 | 9/2008 | O'Malley et al. |
| 2004/0221431 A1 | 11/2004 | Wittmann |
| 2008/0147115 A1 | 6/2008 | O'Malley et al. |
| 2008/0312685 A1* | 12/2008 | O'Malley .............. A61B 17/08 606/216 |
| 2009/0088708 A1* | 4/2009 | Boehringer ........ A61B 17/0466 604/313 |
| 2012/0143225 A1 | 6/2012 | Chin et al. |
| 2014/0235932 A1 | 8/2014 | Ogdahl et al. |

* cited by examiner

IMPLANTABLE FASCIAL APPROXIMATOR

CROSS-REFERENCES TO RELATED APPLICATIONS

This application claims the benefit of U.S. Provisional Patent Application Ser. No. 62/046,241 filed on Sep. 5, 2014, and incorporated herein by reference.

BACKGROUND

In many patients with severe abdominal wall defects, the fascial edges of the defect or incision are retracted too far for primary approximation and closure. In such situations, a closure under too much tension could lead to failure and recurrent hernia. Yet, it is important to finally close the wound.

It has been shown that the biological soft-tissues such as skin and fascia have the capability to stretch with time under external tension. This has been used in rare cases to close large abdominal wall defects. However, external sutures and bands were used for this purpose with associated problems and complications.

SUMMARY

Provided are a plurality of example embodiments of implantable approximators, including, but not limited to, manual and ratchet approximators. Also provided are approximators with automatic tensioning features, including electrically driven devices.

Also provided is a medical device comprising: a body portion; at least one suture configured to connect to tissue of a human or animal patient; at least one gripper device cooperating with the body portion, the gripper device being configured to interact with the suture to pull the suture in a tightening direction to keep the suture under tension for a period of time to provide a pulling force on the tissue to close a wound. The medical device is configured to be placed in the wound of the human or animal patient during operation of the medical device.

Further provided is a medical device comprising: a body portion; at least one pair of sutures each configured to connect to tissue of a human or animal patient; and at least one gripper device cooperating with the body portion, the gripper device including a tension mechanism configured to interact with the sutures to pull the sutures in a tightening direction to keep the sutures under tension for a period of time to provide a pulling force on the tissue to close a wound. The medical device is configured to be placed in the wound of the human or animal patient during operation of the medical device.

Still further provided are any of the disclosed medical devices further comprising an extension portion extending from the body portion, with the extension portion adapted to protrude from the animal for providing access to the medical device after implantation of the medical device in the animal. The extension portion can be adapted to receive a tool with the device being configured to accept the tool for use in pulling the suture to provide the tension.

Also provided are any of the disclosed medical devices where the tensioning mechanism includes a spring, and/or where the tensioning mechanism includes a ratchet mechanism, and/or where the tensioning mechanism is configure to receive a tool for winding the spring to increase tension in the tensioning mechanism, and/or where the tensioning mechanism is configure to wind a portion of a string connected to the suture in a coil within the tensioning mechanism during operation of the tensioning mechanism.

Further provided is a medical device comprising: a body portion; at least one pair of sutures each configured to connect to tissue of a human or animal patient; and at least one gripper device cooperating with the body portion, the gripper device including a tension mechanism having a spring and a ratchet mechanism, the tension mechanism being configured to interact with the sutures to allow the sutures to be pulled in a tightening direction to keep the sutures under tension for a period of time to provide a pulling force on the tissue to close a wound over time; and an extension portion extending from the body portion. The medical device is configured to be implanted in the animal, and the extension portion is adapted to protrude from the animal for providing access to the medical device after placing the medical device in the wound of the human or animal patient. Also, the extension portion is adapted to receive a tool with the device being configured to accept the tool for use in pulling the suture to provide the tension.

Still further provided is a method of performing a medical treatment using any of the medical devices described herein, the method comprising the steps of:
providing the medical device;
connecting one suture to tissue on one side of an incision;
connecting another suture to tissue on another side of the incision;
tightening sutures to put the tension force on the tissue on the sides of the incision using the tension mechanism of the gripper device; and
implanting at least a portion of the medical device in the human or animal patient.

Also provided is a method of performing a medical treatment comprising the steps of:
connecting a first suture to first tissue on one side of a wound of a patient;
connecting a second suture to second tissue on another side of a wound of the patient;
placing a tensioning device within the wound of the patient, wherein the tensioning device is connected to the first suture and the second suture to provide a tensioning force on both sutures for pulling the first tissue and the second tissue together to close the wound over a time period.

Still further provided are any of the above methods further comprising the step of removing the tensioning device from the wound after at least a substantial portion of the wound has closed.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which.

DETAILED DESCRIPTION OF THE EXAMPLE EMBODIMENTS

Figure 1A:
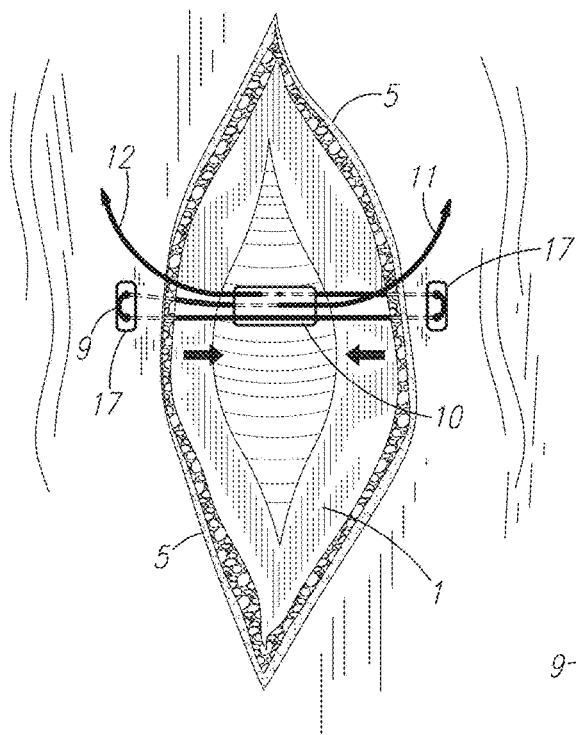
FIG. 1A shows a first example embodiment of a manual approximator operating on an incision.

A desire is for designs of implantable devices and tissue protectors to allow for safer and less morbid fascial reapproximation. Generally, these example devices should be designed to allow a suture connected to animal tissue to be tightened to keep it under tension and thereby pull on the tissue. This can be generally accomplished by allowing the suture to be moved or gathered up in the tensioning direction but then preventing the suture from loosening after it has been tightened. This can be accomplished, as shown by examples provided herein, by using a "gripper device" that acts as a suture "check valve" by gripping and holding the suture, while allowing the suture to be tightened and maintained under tension. Such a device could be a winch, or a ratchet-like device, or a spring device, or a structure similar to those that might be used to tighten a belt or other strap or string device.

Some example embodiments are disclosed to provide a low profile winch-type gripper device which would exert tension, such as a set amount of tension, on a pair of sutures and gradually reduce their length by pulling tissue to close a wound while keeping the tension continuously in place. The device may be configured so that the tension can be increased at certain points in time as the wound closes. By using such an approach, the fascial edges or any other type of tissue which is attached to the suture material, such as two sides of an incision, will be gradually pulled toward the winch, effectively closing the wound over time. In these embodiments, the winch is an example device that applies the force for keeping the tension on the fascial edges.

The winch itself can be a manual device, an electrical device, or purely mechanical device, which may use a spring or ratchet to provide the tension force. For example, the winch may utilized a winding mechanism (e.g., for winding a coil spring) with a ratchet which can be primed prior to implantation, and adjusted periodically to keep the tension in place.

The procedure for using the approximator device involves passing heavy suture material through the healthy portion of the fascia and muscle, and then attaching the suture to the winch, after which the tension can be applied. Alternatively, ends of the suture may be attached to the winch in advance, and the suture "pulled" from the device to extend the suture, thereby putting tension on the suture. To decrease the risk of suture material cutting through the fascia, a set of grommets (metal, Silicon, or biologic materials) can be placed through the tissue first. The sutures are then passed through the grommets. Regardless of the material, each grommet should have a radiologically identifiable marker to identify the grommet on x-rays.

Depending on the length of the defect or incision, one or several winches and associated sutures and, when desired, additional tensioning devices can be placed along the edge of the fascia. In a normal procedure, the skin is closed over the entire mechanism over a period of time, after which the device can be removed, although in some situations removal may occur before the wound has completely closed (e.g., in situations where the wound is nearly closed and further tension is deemed unnecessary). Based on the set speed and the width of the defect, the progress of the extension/approximation is followed with regular X-rays or ultrasound at desired intervals. If manually tightened, a portion of the winch can be exposed through the skin to allow access to tighten the winch, which may also ease removal.

Once the fascial edges are fully approximated, mostly approximated, or at least substantially approximated, during a second procedure the winches are removed (excised) and the sutures are used to close the fascia. Additional sutures may be needed, or the original sutures may be replaced with new sutures, to close the resulting incision. For some embodiments, a manual ratchet can be provided with biologically dissolvable materials which can be degraded slowly by the body and the fascial structures can then scar and heal in the final position without the need for a second procedure.

In one example embodiment, the winch mechanism can be configured to have an adjustable tension, to control the "speed" of the wound closure. A desired "speed" can be set based on the position of the winch in the defect and the width of the opening, thereby varying the tension for increase when greater speed is desired. By performing such an operation, the entire length of the wound is approximated in a homogenous fashion along the elliptic shaped defect, thereby closing the wound over time.

This concept can also be realized as a manual version. The sutures and grommet may remain the same. The central device functions as a unidirectional clamp on the sutures which are passed through it. The free ends of the sutures are delivered to the surface of the skin lateral to the open wound and fascial defect. At given intervals, the exposed ends of the sutures can be manually pulled in opposite directions (e.g., by a technician or nurse or doctor) to achieve tightening of the fascia and narrowing of the defect. The approximator allows the movement of the sutures in one direction only. Thus, there will not be any tension on the free end of the sutures on the skin, obviating the need for an anchoring mechanism at those points.

Figure 1B:
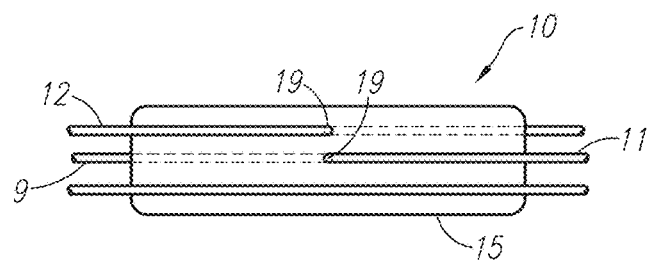
FIG. 1B shows a close-up of a manual approximator for use in the first example embodiment.
Figure 1C:
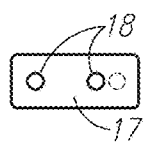
FIG. 1C shows an example grommet for use in the first example embodiment.

FIG. 1A shows a schematic of an example embodiment of a manual approximator 10 for closing a fascia 5. FIG. 1B shows a close-up of the manual approximator 10. A suture 9 is provided connected to the approximator base 15 and which passes through grommets 17 with holes 18 that are attached to the tissue of the patient. FIG. 1C shows a close-up of the grommet 17. Suture ends 11, 12 of the suture 9 are provided in a manner adapted for being pulled through the base 15 to provide tension in the suture 9 for gradually closing the fascia 5.

Suture gripper portions 19 are provided in the base 15 to act as a gripper device for allowing the suture ends 11, 12 to be pulled only in a tightening direction through the base 15, keeping the tension force on the suture 9. The base 15 might be provided of a stretchable material such as a rubber or rubber-like material to help keep the tension force in place.

Example gripper portions 19 could utilize one of many different mechanisms which can provide only a one-way travel for the sutures 9, such as by using a metal or plastic clip gripper 19' having a base portion 21 and tab portions 22 that dig into the suture 9 in one direction preventing flow in that direction, but allows the suture to be pulled out in the other direction. Other types of gripper portions could be used as well. In this example, the gripper portions act both to grip the suture, and to keep the sutures under tension through the elastic properties of the sutures themselves, the base, and even the tissue itself.

Figure 1D:
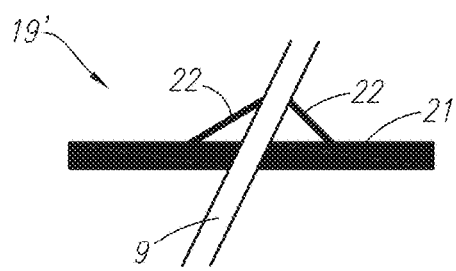
FIG. 1D shows an example of a gripper portion.
Figure 2:
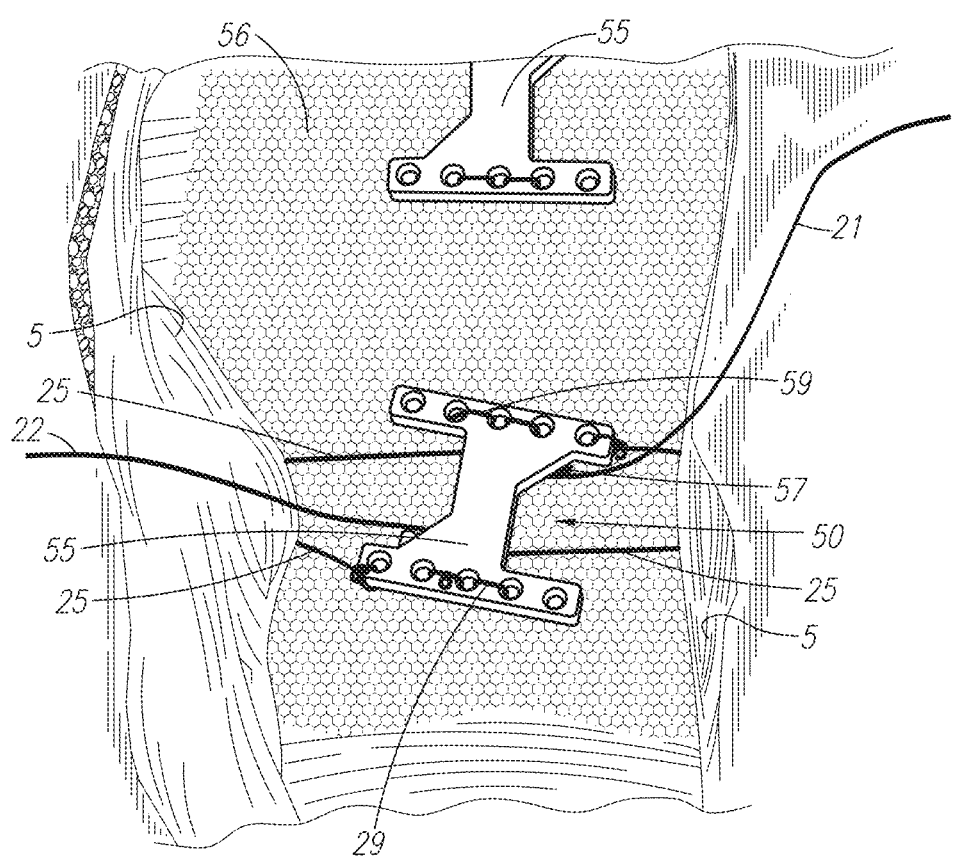
FIG. 2 shows a second example embodiment of a manual approximator.

FIG. 2 shows a second example embodiment of a manual approximator 50 for closing the fascia 5. Mesh 56 is provided to keep the abdominal content in place. Suture 25 is provided with suture ends 21, 22 for manually tightening the suture 25 through the approximator base 55. Other portions of the suture 25 are attached to the fascia 5. Gripper devices 57 are provided under the base 55 to keep the suture 25 tight and preventing the suture from moving in the opposite direction, keeping the suture 25 under tension. Example gripper devices 57 can be comprised of rubber posts (or as shown in FIG. 1D) and are adapted to not allow knots in the suture to move back through the approximator. In other words, the knots can move in one direction through the base and bend the rubber post as the knot passes through. The thinner portion of the suture is pushed to the narrower opening in the base which does not allow the knots to pass back through the base. Additional sutures 59 can be provided and secured to the mesh 56 or the tissue keep the approximator 50 in a desired position.

Figure 3A:
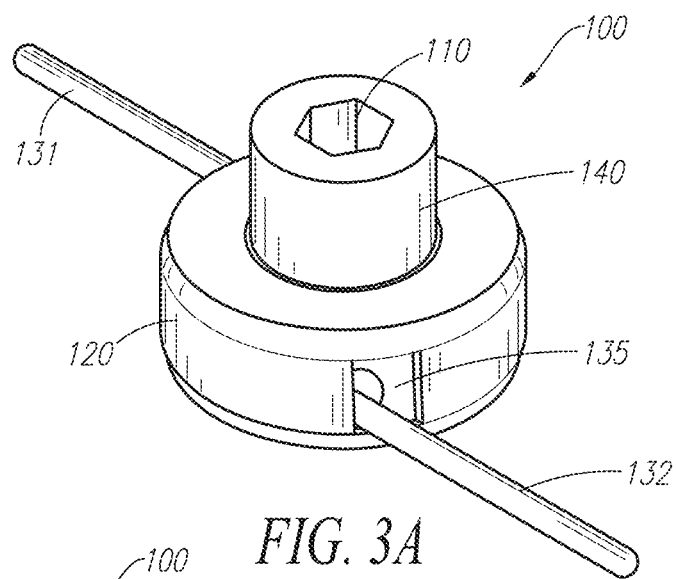
FIGS. 3A-3C show a first example embodiment of a ratchet approximator.
Figure 3B:
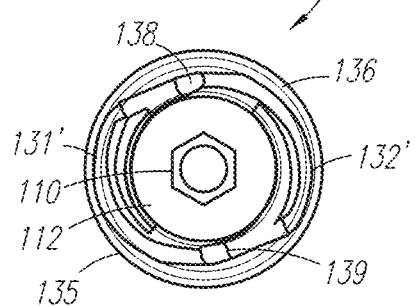
Figure 3C:
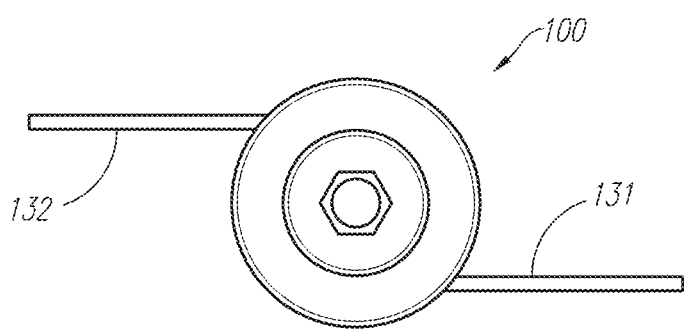

FIGS. 3A, 3B, and 3C show various views of a first example ratcheting winch approximator 100 that uses a ratchet mechanism as a gripper device to provide the tension force and that winds the suture thread into a coil within the mechanism during operation or prior to deployment. The approximator 100 has a hex receptacle 110 provided on a hex body 140, with the hex receptacle 110 being configured to receive a hex (allen) wrench (key) to manually tighten the winch, as desired. Alternative embodiments could be adapted to receive tools other than hex wrenches, such as screw drivers, socket wrenches, etc. The hex body 140 forms an extension portion that extends from the device, and as such can protrude from the skin to allow access while the winch base 120 with bottom 150 and suture connectors 131, 132 can be implanted in the patient (under the skin). In this example, coiled suture threads 131', 132' are shown with the suture connectors 131, 132 which are coiled (wound) within the winch base 120.

The suture connectors 131, 132 are adapted to connect to the sutures 131', 132' which are then to be used for connecting to the fascial edges of the wound (or incision), or they can be end parts of the sutures themselves, being connected to the sutures by knots, for example. The suture connectors 131, 132 are connected to end fasteners 138, 139 that connect to a ratchet disk 125 at connecting points 127, 128, which comprise holes in the ratchet disk 125 for receiving ends of the end fasteners 138, 139. A coil spring (not shown, but can be similar to that shown in FIG. 4B), or other device can be provided to supply tension to the sutures.

Figure 4A:
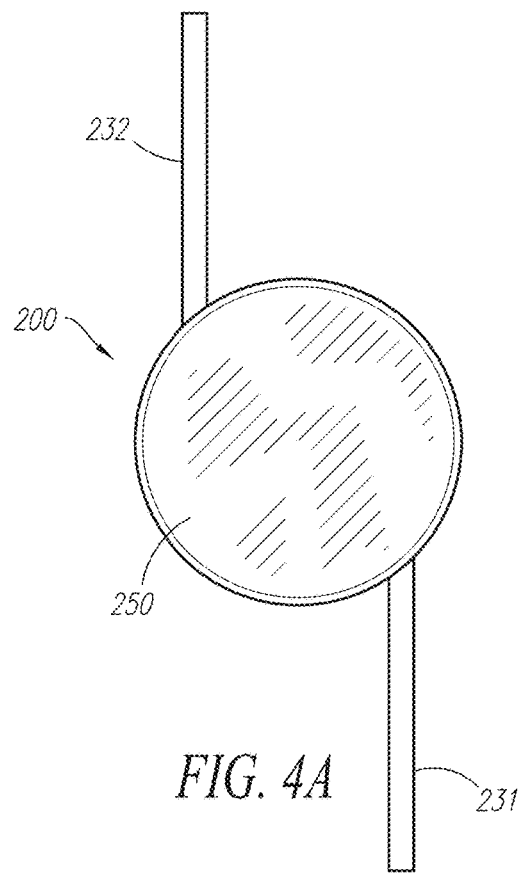
FIGS. 4A-4B show a second example embodiment of a ratchet approximator.
Figure 4B:
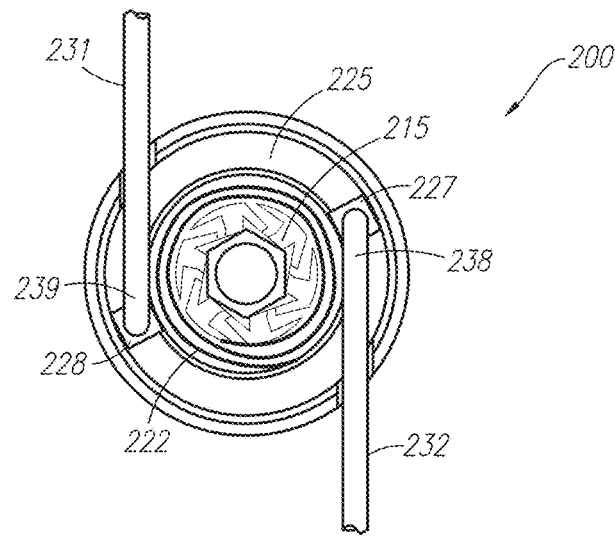

FIGS. 4A and 4B show a second example embodiment of a ratcheting winch approximator 200 also using a ratchet mechanism as a gripper device to provide the tension force where the suture thread remains primarily outside the device. FIG. 4A shows a bottom of the device with sutures 232, 231 extending from the device, and FIG. 4B shows an interior of the device to show internal structure. A top of the device can be made similar to as shown in FIG. 3A. The approximator 200 has a hex receptacle 210 provided on a hex body 240, with the hex receptacle 210 being configured to receive a hex (allen) wrench (key) to manually tighten the winch, as desired (not shown, but can be similar to that shown in FIG. 3B. Alternative embodiments could be adapted to receive tools other than hex wrenches, such as screw drivers, socket wrenches, etc. The hex body 240 forms an extension portion that extends from the device, and as such can protrude from the skin to allow access while the winch base 220 with bottom 250 and suture connectors 231, 232 can be placed in the wound of the patient (e.g., within the wound between the fascia and/or implanted under the skin), eventually to be partially or totally covered by tissue as the wound closes.

Ratchet mechanism 215 is of a design known in the art and is provided to support a ratchet function that allows the ratchet disk 225 to be rotated in one direction to turn the suture connectors 231, 232 around the winch core 112 to provide tension on the sutures, and to prevent the ratchet disk from rotating in the opposite direction. Coil spring 222 is provided to supply a rotational force on the ratchet disk 225 to rotate the suture connectors 231, 232 that are connected to the disk 225 via connector ends 238, 239, and thereby provide the desired tension on the sutures. A similar coil spring and/or ratchet mechanism could be used for the example embodiment of FIGS. 3A-3C as well. Other types of springs as described herein could also be utilized.

Note that in situations where the size of the wound makes it desirable, a plurality of approximator devices may be installed to ensure wound closure in a complete and uniform manner.

The example approximator devices shown in FIGS. 3A-3C and 4A-4B are considered medium sized devices, such as, for example, one with a 30 mm diameter housing, 120 mm total thread (suture) length using a 2 mm diameter thread. At least two other sizes of approximators can be provided: a larger version with 240 mm thread and 36 mm housing diameter; and a smaller version with 60 mm thread and a 24 mm housing diameter. Depending on the clinical demand, devices with longer suture lengths can be used. These approximators can be provided in a compact self-contained manner with the suture threads wound within the device in a manner allowing the sutures to be pulled out of the device (unwound) prior to the device being activated for one-way tightening.

As an alternative, the ratchet mechanism 215 can be supplemented or replaced with an additional coil spring or another spring design provide supplemental tensioning of the device. If a coil spring is used along with a ratchet, the spring can be provided in an unwound (non-tensioned) state during installation of the winch with the sutures, and then the spring can be "wound" like winding a watch spring using the hex receptacle 210 with hex key to apply the tension. For this alternative embodiment, fewer tightening procedure would be necessary, although periodic winding of the spring may be necessary in certain applications to ensure constant tension.

Other alternative embodiments may dispense with the use of the ratchet and winding functions. For example, a linear spring or an electric motor or solenoid could be used to provide the tension force in place of the ratchet and coil spring. Power for an electric device could be provided in an embedded battery, or by using a connection to an external battery that may be worn by the patient.

Figure 5:
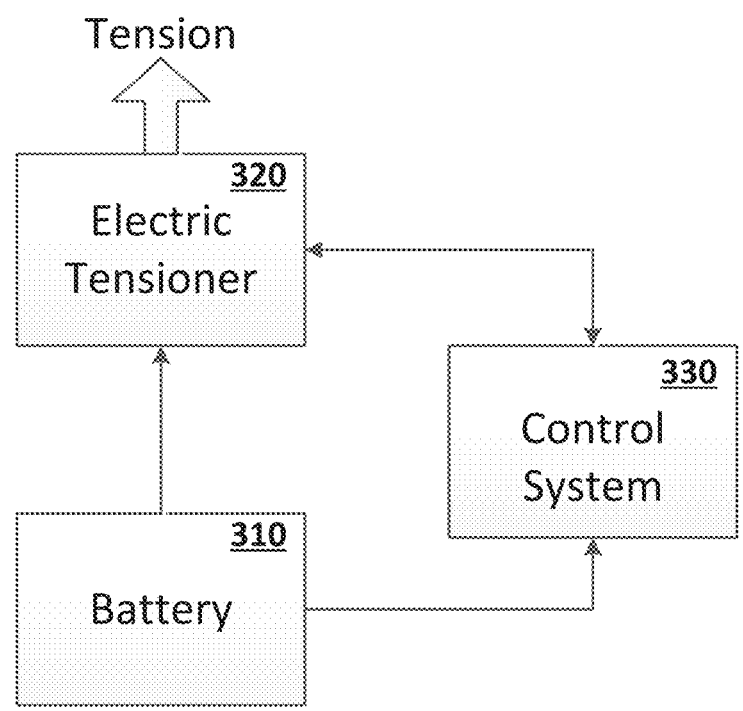
FIG. 5 shows a block diagram of a tensioner with automatic tensioning.

When using an electrically powered source of tension such as a motor or solenoid, the tensioning process can be automated, avoiding the need of a surgeon or technician to regularly tighten the device to maintain the desired tension. A battery can be provided in or near the device to power the source of tension, and a control system (e.g., a computer, controller, or other control device) can be provided on the device, or remote to the device (e.g., connecting wirelessly), to monitor and control the tension as desired, to keep the tension within the desired range(s). FIG. 5 is a block diagram showing such a structure, with a battery 310, electric tensioner 320, and control system 330 to monitor and automatically control the tension. The battery and/or control system can be included internal to the device housing, or as an external component wired to the device. The desired tension can be pre-set by a physician, for example, and thereby automatically adjust as the fascia closes the wound.

Generally, the devices are utilized by attaching the sutures to the fascia and attaching the sutures to the approximator in the appropriate manner depending on the embodiment of the approximator chosen. The approximator can then be tensioned and implanted in the patient (e.g., under the skin) as desired, with a portion of the approximator extending from the skin to allow access for manual tightening, if required of that approximator embodiment. Once the fascia are sufficiently closed (e.g., once the fascial edges are fully approximated, mostly approximated, or at least substantially approximated) during a removal procedure the approximator is surgically removed and the wound is closed in the desired manner.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A medical device comprising:
    a body portion;
    at least one pair of sutures comprising a first suture and a second suture, each configured to connect to tissue of a human or animal patient;
    at least one gripper device cooperating with the body portion, the gripper device including a tensioning mechanism having a spring and a ratchet mechanism, the tensioning mechanism being configured to interact with the first suture and the second suture to allow the first suture to be pulled in a first tightening direction and the second suture to be pulled in a second tightening direction opposite the first tightening direction to keep the first suture and the second suture under tension for a period of time to provide a pulling force on the tissue to close a wound over time; and
    an extension portion extending from the body portion, wherein
    the medical device is configured to be implanted in the human or animal, and further wherein
    the extension portion is adapted to protrude from the human or animal for providing access to the medical device after placing the medical device in the wound of the human or animal patient, and wherein
    the extension portion is adapted to receive a tool with the medical device being configured to accept the tool for use in pulling the first suture and the second suture to provide the tension.

2. The medical device of claim 1, wherein the tensioning mechanism is configured to receive the tool for winding the spring to increase tension in the tensioning mechanism.

3. The medical device of claim 1, wherein the tensioning mechanism is configured to wind a portion of a first string connected to the first suture and a second string connected to the second suture in a coil within the tensioning mechanism during operation of the tensioning mechanism.

4. The medical device of claim 1, further comprising a control system and power source connected to the tensioning mechanism, wherein the medical device is configured to automatically monitor and adjust tension.

* * * * *